US010825565B2

(12) United States Patent
Reddy

(10) Patent No.: US 10,825,565 B2
(45) Date of Patent: Nov. 3, 2020

(54) SYSTEM AND METHOD FOR VALIDATING MEDICAL CLAIM DATA

(71) Applicant: SYNTEL, INC., Troy, MI (US)

(72) Inventor: Murlidhar Reddy, Maharashtra (IN)

(73) Assignee: SYNTEL, INC., Troy, MI (US)

( * ) Notice: Subject to any disclaimer, the term of this patent is extended or adjusted under 35 U.S.C. 154(b) by 1044 days.

(21) Appl. No.: 14/306,077

(22) Filed: Jun. 16, 2014

(65) Prior Publication Data

US 2014/0372140 A1 Dec. 18, 2014

Related U.S. Application Data

(60) Provisional application No. 61/834,908, filed on Jun. 14, 2013.

(51) Int. Cl.
| | |
|---|---|
| *G16H 40/20* | (2018.01) |
| *G06Q 50/22* | (2018.01) |
| *G06F 8/70* | (2018.01) |
| *G06F 8/30* | (2018.01) |
| *G16H 10/60* | (2018.01) |

(52) U.S. Cl.
CPC .............. *G16H 40/20* (2018.01); *G06F 8/30* (2013.01); *G06F 8/70* (2013.01); *G06Q 50/22* (2013.01); *G16H 10/60* (2018.01)

(58) Field of Classification Search
CPC ........ G06Q 50/22; G06Q 50/24; G16H 10/60; G16H 40/20; G06F 8/70; G06F 8/30
USPC ........................................................ 705/2–3
See application file for complete search history.

(56) References Cited

U.S. PATENT DOCUMENTS

| | | |
|---|---|---|
| 4,558,413 A | 12/1985 | Schmidt et al. |
| 5,018,067 A | 5/1991 | Mohlenbrock et al. |
| 6,493,871 B1 | 12/2002 | McGuire et al. |
| 6,785,410 B2 | 8/2004 | Vining et al. |
| 7,233,938 B2 | 6/2007 | Carus et al. |
| 7,437,302 B2 | 10/2008 | Haskell et al. |
| 7,546,595 B1 | 6/2009 | Wickham et al. |
| 7,861,239 B2 | 12/2010 | Mayfield et al. |
| 8,265,952 B1 | 9/2012 | Smith |
| 8,370,799 B2 | 2/2013 | Nir-Buchbinder et al. |
| 8,428,970 B1 * | 4/2013 | Fiferlick ............ G06Q 30/0185 705/3 |
| 2003/0069760 A1 | 4/2003 | Gelber |
| 2003/0191665 A1 * | 10/2003 | Fitzgerald .............. G16H 50/20 705/2 |

(Continued)

OTHER PUBLICATIONS

Quest Software, Toad for Oracle User Guide 10, 2009, Quest Software, pp. 1-8, 185-186, 197 (Year: 2009).*

(Continued)

*Primary Examiner* — Joy Chng
(74) *Attorney, Agent, or Firm* — Miles & Stockbridge, P.C.

(57) ABSTRACT

A system for validating medical claim data receives a first and second medical claim, each respectively associated with a first and a second healthcare classification system, receives claim edit criteria, stores the first and second medical claims in association with the first and the second classification systems, respectively, validates the stored medical claims by applying the received claim edit criteria to one of the stored medical claims and to the associated classification system, and graphically displays selected results of the validating.

21 Claims, 10 Drawing Sheets

(56) References Cited

U.S. PATENT DOCUMENTS

| | | | |
|---|---|---|---|
| 2004/0172291 A1* | 9/2004 | Knowlton | G06Q 50/22 705/2 |
| 2005/0038670 A1 | 2/2005 | Takkar et al. | |
| 2005/0137912 A1 | 6/2005 | Rao et al. | |
| 2007/0027720 A1* | 2/2007 | Hasan | G06Q 50/24 705/3 |
| 2008/0195999 A1 | 8/2008 | Cohen et al. | |
| 2009/0150181 A1 | 6/2009 | Gejdos et al. | |
| 2009/0164252 A1 | 6/2009 | Morris et al. | |
| 2010/0094657 A1 | 4/2010 | Stern | |
| 2010/0198799 A1 | 8/2010 | Krishnan et al. | |
| 2011/0301982 A1 | 12/2011 | Green, Jr. et al. | |
| 2012/0078979 A1 | 3/2012 | Ghimire | |
| 2012/0089964 A1 | 4/2012 | Sawano | |
| 2012/0254083 A1* | 10/2012 | Patrao | G16H 15/00 706/14 |
| 2012/0296675 A1 | 11/2012 | Silverman | |
| 2012/0311426 A1 | 12/2012 | Desai et al. | |
| 2013/0035947 A1* | 2/2013 | Sundararam | G06Q 50/22 705/2 |
| 2013/0073301 A1 | 3/2013 | Rao et al. | |
| 2013/0144651 A1 | 6/2013 | Rao | |
| 2013/0185094 A1 | 7/2013 | Mukerji et al. | |
| 2013/0227524 A1 | 8/2013 | Im et al. | |
| 2013/0227533 A1 | 8/2013 | Tonkin et al. | |
| 2014/0136495 A1* | 5/2014 | Kottaram | G06F 16/258 707/695 |

OTHER PUBLICATIONS

Coder Coach: "What the Heck is a DRG? And Why Should I Care About Case Mix?" (Jan. 6, 2011, 5 pgs.).

"Introduction to Network Load Balancing", Network Load Balancing (NLB) (Jan. 21, 2005, 2 pgs.).

"Overview of Network Load Balancing" (Dec. 21, 2007, 3 pgs.).

Ron Mills, "ICD-10-CM/PCS MS-DRG Grouper Part 1" (May 23, 2011, 3 pgs.).

Stein, Brian G., et al., "The Validity of International Classification of Diseases, Ninth Revision, Clinical Modification Diagnosis Codes for Identifying Patients Hospitalized for COPD Exacerbations." CHEST Journal 141.1 (2012), pp. 87-93.

McDonald, Clement J., et al. "Open Source Software in Medical Informatics—Why, How and What." International Journal of Medical Informatics 69.2 (2003), pp. 175-184.

Ayewah, Nathaniel, et al. "Evaluating Static Analysis Defect Warnings on Production Software", Proceedings of the 7th ACM SIGPLAN-SIGSOFT Workshop on Program Analysis for Software Tools and Engineering, ACM, (2007), pp. 1-7.

Final Office Action dated Jun. 3, 2019 in U.S. Appl. No. 14/306,208.

Non Final Office Action dated Apr. 15, 2019 in U.S. Appl. No. 14/306,060.

Final Office Action dated Aug. 1, 2019 in U.S. Appl. No. 14/306,060.

Notice of Allowance dated Sep. 30, 2019 in U.S. Appl. No. 14/306,208.

3M "Advanced Analyzer Software" Apr. 2013 (Year: 2013).

De, Suman "8 Steps to Success in ICD-10-CM/PCS Mapping: Best Practices to Establish Precise Mapping Between Old and New ICD Code Sets" as downloaded from http://library.ahima.org/doc?oid= 106975 Journal of AHIMA 83, No. 6 (Jun. 2012): 44-49. (Year: 2012).

3M TM "Coding and Reimbursement System" Published Apr. 2013 (Year: 2013).

CMS, "General Equivalence Mappings—ICD-9-CM to and from ICD-10-CM and ICD-10-PCS" Mar. 2009 (Year: 2009).

Cognizant, "ICD Code Crosswalks: No Substitute for ICD-10 Compliance" cognizant 20-20 insights I May 2013 (Year: 2013).

Non Final Office Action dated Jan. 28, 2020 in corresponding U.S. Appl. No. 14/306,060.

* cited by examiner

| CLAIM RECORDNO | MEMBER ID | AGE | GENDER | DOB | PROVIDER ID | INPATIENT | IN_PLAN | GROUP | PLACE OF | ADMIT DIAG | PROCEDURE | CHARGED |
|---|---|---|---|---|---|---|---|---|---|---|---|---|
| C407507368 | M587453512 | 38 | M | ######## | P540793799 | 1 | 1 | GRP101 | 21 | 414.01 | 0.66 | 13579.91 |
| C407507369 | M587453513 | 14 | M | ######## | P942854057 | 1 | 1 | GRP101 | 21 | 414.01 | 0.66 | 13053.58 |
| C407507370 | M587453514 | 39 | F | ######## | P430652656 | 1 | 0 | GRP101 | 21 | 414.01 | 0.66 | 7644.75 |
| C407507371 | M587453515 | 72 | M | ######## | P250969492 | 1 | 0 | GRP104 | 21 | 414.01 | 0.66 | 9083.99 |

FIG. 9A

| CLAIM RECORD | CLAIM LINE | TYPE OF SERV | PLACE OF SERVICE | FIRST DATE OF | LAST PROCED | REVENUE | CPT HCPCS | NO OF UNITS | CHARGED | ALLOWED | PAID AMO |
|---|---|---|---|---|---|---|---|---|---|---|---|
| C407507368 | 1 | | 600 | 21 | 9/16/2011 | 9/19/2011 | 112 | | 3 | 4770.17 | |
| C407507369 | 2 | | 600 | 21 | 7/3/2011 | 7/7/2011 | 255 | | 4 | 1402.92 | |
| C407507370 | 3 | | 600 | 21 | 7/29/2011 | 8/1/2011 | 321 | | 3 | 3543.78 | |
| C407507371 | 4 | | 600 | 21 | 7/12/2011 | 7/17/2011 | 305 | | 5 | 3863.04 | |

FIG. 9B

| PLAN ID | PLAN NAME | NETWORK_ID | BENEFITS_ID | EFFECTIVE_DATE | EFFECTIVE_THROUGH | PLAN_TYPE | PREEXISTING | SPOUSE_BENEFITS | OTHER_DEPENDENTS BENEFITS |
|---|---|---|---|---|---|---|---|---|---|
| BP100 | SaraJeevan | Network4 | Benefits3 | 1/1/2009 0:00 | 1/1/2010 0:00 | H | PREId2 | Benefits3 | Benefits3 |
| BP101 | PrudentialLife | Network1 | Benefits1 | 1/1/2009 0:00 | 1/1/2010 0:00 | H | PREId2 | Benefits1 | Benefits1 |
| BP102 | BUPAMaxLife | Network1 | Benefits1 | 1/1/2009 0:00 | 1/1/2010 0:00 | S | PREId2 | Benefits1 | Benefits1 |
| BP104 | SaveLife | Network1 | Benefits4 | 1/1/2009 0:00 | 1/1/2010 0:00 | S | PREId1 | Benefits4 | Benefits4 |
| BP200 | StandardLife | Network2 | Benefits1 | 1/1/2009 0:00 | 1/1/2010 0:00 | S | PREId1 | Benefits1 | Benefits1 |
| BP201 | JeevanAnand | Network3 | Benefits2 | 1/1/2009 0:00 | 1/1/2010 0:00 | S | PREId1 | Benefits2 | Benefits2 |
| BP203 | BlueCrossPlatinum | Network3 | Benefits2 | 1/1/2009 0:00 | 1/1/2010 0:00 | H | PREId1 | Benefits2 | Benefits1 |
| BP301 | PPOSuperLife | Network1 | Benefits1 | 1/1/2009 0:00 | 1/1/2010 0:00 | H | PREId3 | Benefits1 | Benefits2 |
| BP302 | PPOStandardLife | Network2 | Benefits2 | 1/1/2009 0:00 | 1/1/2010 0:00 | H | PREId3 | Benefits2 | Benefits1 |
| BP303 | HMOTitaniumPlus | Network3 | Benefits3 | 1/1/2009 0:00 | 1/1/2010 0:00 | H | PREId4 | Benefits3 | Benefits3 |
| BP034 | POSTitaniumPlus | Network4 | Benefits4 | 1/1/2009 0:00 | 1/1/2010 0:00 | H | PREId4 | Benefits4 | Benefits4 |

FIG. 10A

| Diagnosis_Code_From | Diagnosis_Code_To | Procedure_Code_From | Procedure_Code_To | Age_Min | Age_Max | Gender | Revenue_Code_From | Revenue_Code_To |
|---|---|---|---|---|---|---|---|---|
| 120.8 | 120.8 | 99244 | | | | | | |
| 120.8 | 120.8 | 81000 | | | | | | |
| 197.2 | 197.2 | 97002 | | | | | | |
| 189.0 | 189.0 | 97002 | | | | | | |
| 189.1 | 189.1 | 97002 | | | | | | |
| Z98.52 | Z98.92 | | | 15 | 124 | | | |
| A18.16 | A18.16 | | | | | F | | |

FIG. 10B

| Benefits_Id | Service_Id | Dependent | Out_Network | AgeMin | AgeMax | Gender | INN-Copay | INN-Coins | INN_Ind_Ded | OON_Copay | OON_Coins | OON_Ind_Ded |
|---|---|---|---|---|---|---|---|---|---|---|---|---|
| Benefits1 | AS101 | TRUE | TRUE | 0 | 99 | B | 100 | 10 | 500 | 100 | 10 | 500 |
| Benefits1 | DG101 | TRUE | TRUE | 0 | 99 | B | 100 | 10 | 500 | 100 | 10 | 500 |
| Benefits1 | DL101 | TRUE | TRUE | 0 | 99 | B | 100 | 10 | 500 | 100 | 10 | 500 |
| Benefits1 | ER101 | TRUE | TRUE | 0 | 99 | B | 100 | 10 | 500 | 100 | 10 | 500 |

FIG. 10C

SYSTEM AND METHOD FOR VALIDATING MEDICAL CLAIM DATA

CROSS-REFERENCE TO RELATED APPLICATION

This application claims the benefit of, and priority to, U.S. Patent Application Ser. No. 61/834,908, filed Jun. 14, 2013, the disclosure of which is incorporated herein by reference in its entirety.

FIELD OF THE INVENTION

This disclosure relates generally to a computerized system and method for healthcare-related data, and more specifically to a system and method for validating medical claim data following migration to a new health care coding classification system.

BACKGROUND

Healthcare legislation specifies procedures for communicating information within the healthcare industry. For example, Title II (Administrative Simplification provisions) of the Health Insurance Portability and Accountability Act of 1996 ("HIPAA") required the Department of Health and Human Services to establish national standards for electronic health care transactions and national identifiers for providers, health plans, and employers.

On Jan. 1, 2012, an updated version of the healthcare transactions standard, HIPAA 5010, replaced version 4010A1, the current set of standards. Among various changes in this update, HIPAA 5010 mandates changes to the International Classification of Diseases ("ICD"), which is a nomenclature for the classification of diseases, injuries, and other medical conditions. More specifically, HIPAA 5010 requires healthcare payers and providers to transition from the current International Classification of Diseases, 9th Revision, Clinical Modification ("ICD-9") to a 10th revision ("ICD-10"). This transition is referred to herein as the "ICD-10 migration" and, at present, all healthcare stakeholders (e.g., providers, payers, and employers), must make this transition by Oct. 1, 2015.

ICD-10 codes exhibit fundamental differences as compared with ICD-9 codes. For example, the form and information conveyed in ICD-10 codes is different than that of the ICD-9 codes. More specifically, ICD-9 codes contain three to five digits beginning with either a number or a letter, with a decimal point placed after the third digit, and the ICD-9 book indicates the level of specificity for each code. ICD-10 codes, on the other hand, are seven digits in length. The first three digits of the ICD-10 codes are similar to the ICD-9 codes, with a decimal point after the third digit. However, the digits that follow the decimal point have different, specific meanings. For medical and surgical procedures, for example, the digits that follow are specific to body part, surgical approach, and other qualifiers needed for billing. Similarly, the ICD-10 codes that represent diagnosis codes also have seven digits.

The first three digits of ICD-10 codes are similar to the ICD-9 code, but the additional digits add specificity to the code such as laterality, chronic versus acute, and so on. Another significant difference between the ICD-9 and ICD-10 code sets is the number of codes. More specifically, ICD-9 includes just over 14,000 diagnosis codes and almost 4,000 procedural codes. In contrast, ICD-10 contains over 68,000 diagnosis codes (clinical modification codes) and over 72,000 procedural codes. Due to such fundamental differences, mapping or translation from the ICD-9 code set to the ICD-10 code set presents challenges to ICD-10 migration. For example, while there are some one-to-one correspondences between ICD-9 and ICD-10 codes, there are also one-to-many, many-to-one and many-to-many correspondences and, in some cases, no correspondence at all. Accordingly, ICD-10 migration will undoubtedly affect many aspects of information collection, reporting requirements, billing and payment systems, potentially resulting in benefit, financial and clinical variations.

SUMMARY

The present invention may comprise one or more of the features recited in the attached claims, and/or one or more of the following features and combinations thereof. In one aspect, a computerized method for validating medical claim data comprises receiving a first and second medical claim, each respectively associated with a first and a second healthcare classification system, receiving claim edit criteria, storing the first and second medical claims in association with the first and the second classification systems, respectively, validating the stored medical claims by applying the received claim edit criteria to one of the stored medical claims and to the associated classification system, and graphically displaying selected results of the validating.

In another aspect, a system for validating medical claim data of a member comprises one or more computing devices including a memory having program code stored therein and a processor in communication with the memory for carrying out instructions in accordance with the stored program code, wherein the program code, when executed by the processor, causes the processor to receive a first and second medical claim, each respectively associated with a first and a second healthcare classification system, receive claim edit criteria, store the first and second medical claims in association with the first and the second classification systems, respectively, validate the stored medical claims by applying the received claim edit criteria to one of the stored medical claims and to the associated classification system, and graphically display selected results of the validating.

In a further aspect, a computer program product comprising non-transitory computer readable medium further comprises code for receiving a first and second medical claim, each respectively associated with a first and a second healthcare classification system, code for receiving claim edit criteria, code for storing the first and second medical claims in association with the first and the second classification systems, respectively, code for validating the stored medical claims by applying the received claim edit criteria to one of the stored medical claims and to the associated classification system, and code for graphically displaying selected results of the validating.

In still a further aspect, a system for validating medical claim data comprises a first module to receive a first and second medical claim, each respectively associated with a first and second healthcare classification system, and for receiving claim edit criteria, a second module to validate the first and second medical claims by applying the received claim edit criteria to one of the first and second medical claims and to the associated classification system, and a third module to graphically display selected results of the validating.

BRIEF DESCRIPTION OF THE DRAWINGS

This disclosure is illustrated by way of example and not by way of limitation in the accompanying FIG.s. Where considered appropriate, reference labels have been repeated among the FIG.s to indicate corresponding or analogous elements.

FIG. 9A is an example of selected columns of a claim in header format according to embodiments of the present disclosure.

FIG. 9B is an example of selected columns of a claim in a line format according to embodiments of the present disclosure.

FIG. 10A is an example of benefit edit claim criteria according to embodiments of the present invention.

FIG. 10B is an example of clinical edit claim criteria according to embodiments of the present invention.

FIG. 10C is an example of financial edit claim criteria according to embodiments of the present invention.

DETAILED DESCRIPTION OF THE DRAWINGS

Figure 1:
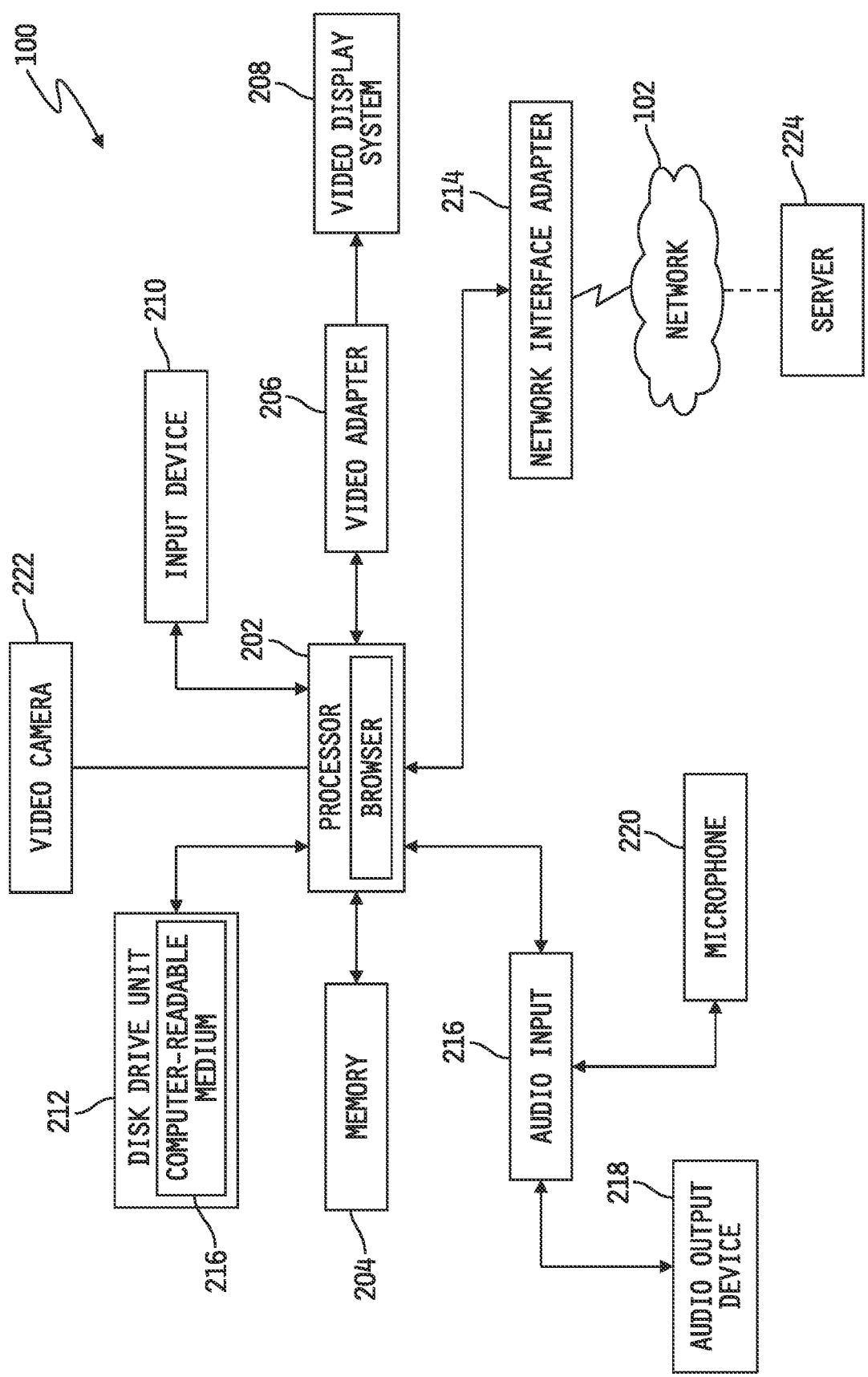
FIG. 1 is a simplified block diagram of an embodiment of a computerized system that may be programmed with a set of instructions to perform any one or more of the functions, processes and methods discussed herein.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

This application relates to the following applications all filed on even date herewith, the disclosures of which are incorporated herein by reference in their entirety; U.S. patent application Ser. No. 14/306,060, entitled System and Method for Providing Mapping Between Different Disease Classification Codes, U.S. patent application Ser. No. 14/306,208, (now U.S. Pat. No. 10,607,733) entitled System and Method for Ensuring Medical Benefit Claim Payment Neutrality Between Different Disease Classification Codes, U.S. patent application Ser. No. 14/306,026, (now U.S. Pat. No. 9,268,907) entitled System and Method for Automatically Modifying Source Code to Accommodate a Software Code Migration, and U.S. patent application Ser. No. 14/305,994, (now U.S. Pat. No. 9,898,582), entitled System and Method for Analyzing an Impact of a Software Code Migration.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases may or may not necessarily refer to the same embodiment. Further, when a particular feature, structure, process, process step or characteristic is described in connection with an embodiment, it is submitted that it is within the knowledge of one skilled in the art to effect such feature, structure, process, process step or characteristic in connection with other embodiments whether or not explicitly described. Further still, it is contemplated that any single feature, structure, process, process step or characteristic disclosed herein may be combined with any one or more other disclosed feature, structure, process, process step or characteristic, whether or not explicitly described, and that no limitations on the types and/or number of such combinations should therefore be inferred.

Embodiments of this disclosure may be implemented in hardware, firmware, software, or any combination thereof. Embodiments of this disclosure implemented in a computer system may include one or more bus-based interconnects between components and/or one or more point-to-point interconnects between components. Embodiments of this disclosure may also be implemented as instructions stored on one or more machine-readable media, which may be read and executed by one or more processors. A machine-readable medium may be embodied as any device or physical structure for storing or transmitting information in a form readable by a machine (e.g., a computing device). For example, a machine-readable medium may be embodied as any one or combination of read only memory (ROM); random access memory (RAM); magnetic disk storage media; optical storage media; flash memory devices; and others.

Referring now to FIG. 1, an embodiment is shown of a system 100 for validating medical claim data based on ICD-9 and/or ICD-10 code sets. Although a migration from ICD-9 to ICD-10 is discussed herein for purposes of example, this disclosure is not intended to be limited to migration from ICD-9 to ICD-10, but encompasses migration from any one medical classification system to another medical classification system. The computing device 100 may be a personal computer, a tablet computer, a personal digital assistant ("FDA"), a media player, a cellular telephone, or any machine capable of executing a set of instructions (sequential or otherwise) that specify actions to be taken. The system 100 according to embodiments of the present disclosure may include a processor 202 (e.g., a central processing unit ("CPU")), a memory 204, a video adapter 206 that drives a video display system 208 (e.g., a liquid crystal display ("LCD"), a cathode ray tube ("CRT"), a touch screen), an input device 210 (e.g., a keyboard, mouse, touch screen display, etc.) for the user to interact with the program (e.g., browser), a disk drive unit 212, a network interface adapter 214, an audio in/out jack 216 that allows audio to be outputted/received by an audio output device 218 (e.g., speaker, headphones) and microphone 220, respectively. Although a combined audio in/out jack 216 is shown for purposes of example, one skilled in the art should appreciate that separate devices may be provided for input and output of audio. It will be understood that that various embodiments of the computing device 100 may not always include all of these peripheral devices, and may instead include various subsets thereof. It will further be understood that the video display system 208 may, in some embodiments, be provided in the form of one or more conventional display monitors.

The disk drive unit 212 includes a computer-readable medium 216 on which may be stored a program code for a web browser with commonly installed plugin(s), such as Flash™ and/or Java™. In some cases, the browser may provide support for the emerging HTML5 WebRTC standard. Embodiments are also contemplated in which the browser could be on a mobile internet connected device, such as a phone or tablet, which has support for the emerging HTML5 WebRTC standard. In one embodiment, a custom application could be provided on an Internet connected mobile device. The term "computer-readable medium" shall be taken to include, but not be limited to, solid-state memories, optical media, flash memory, and magnetic media. Embodiments are contemplated in which the browser may run applications that are received from a server 224 over a network 102 via the network interface device 214 utilizing any one of a number of transfer protocols including but not limited to the hypertext transfer protocol ("HTTP") and file transfer protocol ("FTP"). The network 102 may be any type of packet-switched data network including but not limited to fiber optic, wired, and/or wireless communication capability in any of a plurality of protocols, such as TCP/IP, Ethernet, WAP, IEEE 802.11, or any other protocol.

When an insured patient (also called a member) wishes to receive payment from a payer to cover some or all of the cost of a medical service or treatment, the insured, or in some cases, the service provider, submits a claim to a payer. The term "payer" is broadly intended to cover any entity that pays for medical services, including both private insurance companies and government agencies. The payer then evaluates the claim, and decides whether it will provide a payment, and, if so, how much of the total charge for the medical service it will pay for. The amount of this payment may be based on many factors including contractual relationships between the payer and a network of healthcare providers, who are accessed by the insured patients.

For billing purposes, the use of healthcare claim codes, such as ICD codes, serves to tell a payer (e.g., insurance company), not only what service has been provided, but also the diagnosis, symptom, complaint, condition or problem (e.g., the reason for performing the service), as well as health care resources used.

This above described payment process (also known as claim adjudication) reviews the information on the claim which includes: ICD codes, dates of service, who received the service, who rendered the service, the specific services or "procedures" rendered, the diagnosis which justifies the medical need for the rendered services, and other related information such as medical history, etc. The process then applies simulated payer policy rules (often referred to as "edits") to the medical claims data.

Due to the reliance on ICD codes, the migration from the currently used ICD-9 codes to ICD-10 codes will greatly affect current billing and payment systems. As such, it is desirable that the payments of benefits based on the ICD-9 and on ICD-10 codes result in minimal or no impact on covered services and member responsible amounts.

An early analysis and study of claim adjudication variations between ICD-9 and ICD-10 may save payers considerable effort post ICD-10 migration. Organizations that have yet to change their systems should conduct benefit neutrality testing in a simulated environment to assess potential risks of the ICD-10 migration, and take preventative actions prior to ICD-10 testing.

Embodiments of the present disclosure include a medical claim validation tool designed to recreate the ICD-9 and ICD-10 edits related to benefit coverage validation and member liability determination. For example, the medical claims data are analyzed for possible errors. Therefore, by applying these edits to medical claims data using the system described herein, organizations can obtain accurate, processed claims with which to perform efficient and accurate neutrality testing.

According to one aspect of the present disclosure, a computerized system and method for validating medical claim data of a member is disclosed. A first and second medical claim may be received. Each of these first and second medical claims is respectively associated with a first and second healthcare classification system. Claim edit criteria may be received. The first and second medical claims in association with the first and second classification systems, respectively, may be stored. The stored medical claims may be validated by applying the received claim edit criteria to the stored medical claims of the associated classification system. The results of the validation may be graphically displayed.

Figure 2:
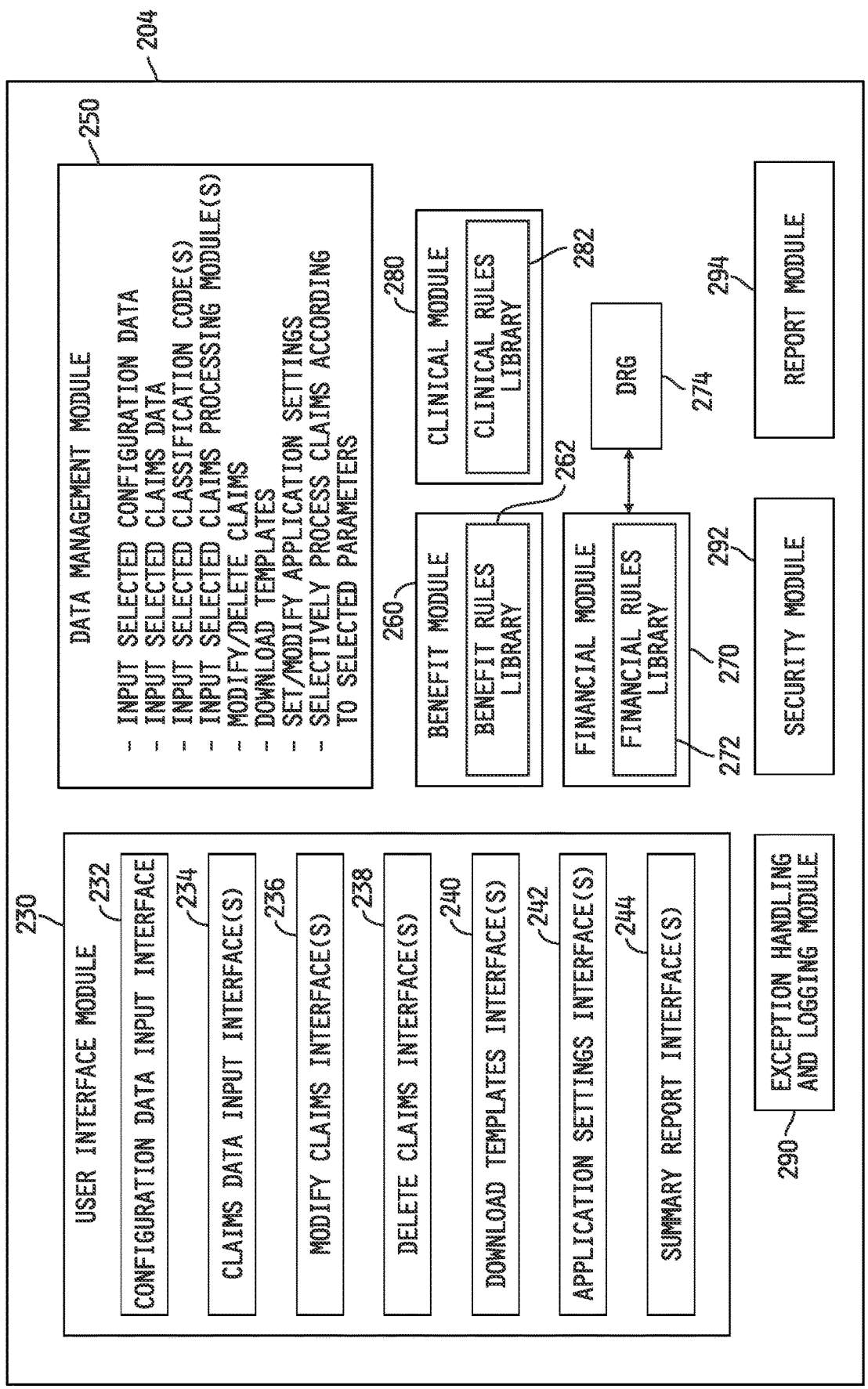
FIG. 2 is a simplified block diagram representation of a software environment of the system illustrated in FIG. 1.

Referring to FIG. 2, a simplified block diagram is shown of a software environment of the system of FIG. 1. In the illustrated embodiment, the medical claim data validation tool is implemented in the form of instructions stored in the memory 204 of the system 100 and executable by the processor 202 to perform the functions described herein. Alternatively or additionally, the instructions may be stored in whole or in part on the computer-readable medium 216, and/or on the server 224 and accessed by the processor 202 via the network 102. Alternatively or additionally still, the server 224 may include one or more processors which execute the instructions, and input/output data may be exchanged between the processor 202 and the server 224 via the network 102. In any case, the medical claim validation tool includes a user interface module 230, a data management module 250, a benefit module 260, a financial module 270, a clinical module 280, an exception handling and logging module 290, a security module 292 and a report module 294.

The user interface module 230 includes a number of graphic user interfaces for receiving user input and for producing reports generated by the medical claim validation tool. In the illustrated embodiment, for example, the user interface module 230 includes one or more configuration data input interfaces 232, one or more claims data input interfaces 234, one or more claims modification interfaces 236, one or more claims deletion interfaces 238, one or more template download interfaces 240, one or more application settings interfaces 242 and one or more summary report interfaces 244. It will be understood that while some embodiments may include all such interfaces, other embodiments may include various subsets of such interfaces.

The data management module 250 manages the input of information to, and user control of, the medical claim validation tool. For example, the data management module 250 illustratively manages the input to the tool of configuration data selected by the user, of claims data selected by the user, of one or more classification codes selected by the user, of one or more claims processing modules selected by the user, of claims modifications and/or deletions made by the user, of the downloading of templates specified by the user and of application setting modifications made by the user. The data management module 250 further initiates the processing of claims by the tool in response to user input.

The benefit module 260 illustratively includes a benefit rules library 262, and is operable to validate the selected medical claims data against the benefit rules contained in the benefit rules library 262. The financial module 270 likewise illustratively includes a financial rules library 272, and is operable to validate the selected medical claims data against the financial rules contained in the financial rules library 272. The financial module 270 illustratively interfaces with a conventional Medical Severity Diagnosis Related Group (MS-DRG) module to extract a DRG interface for conducting DRG calculations in relation to financial edits. The clinical module 280 illustratively includes a clinical rules library 282, and is operable to validate the selected medical claims data against the clinical rules contained in the clinical rules library 282. As will be described in greater detail hereinafter, the benefit module 260, the financial module 270 and the clinical module 280 are all separate from each other and individually selectable by the user such that the tool may be configured by the user to validated the medical claims data selected by the user against one or any combination of the benefits rules, the financial rules and the clinical rules.

The exception handling and logging module 290 operates to handle data access and logic exceptions, and to log such exceptions into a log file contained in memory. The security module 292 operates to restrict access to and functionality of the tool based on assigned user roles. In one embodiment, the security module 292 is implemented with Windows® Authentication using Active Directory. The report module 294 operates to generate one or more reports of the results of the claims validation process(es).

Figure 3:
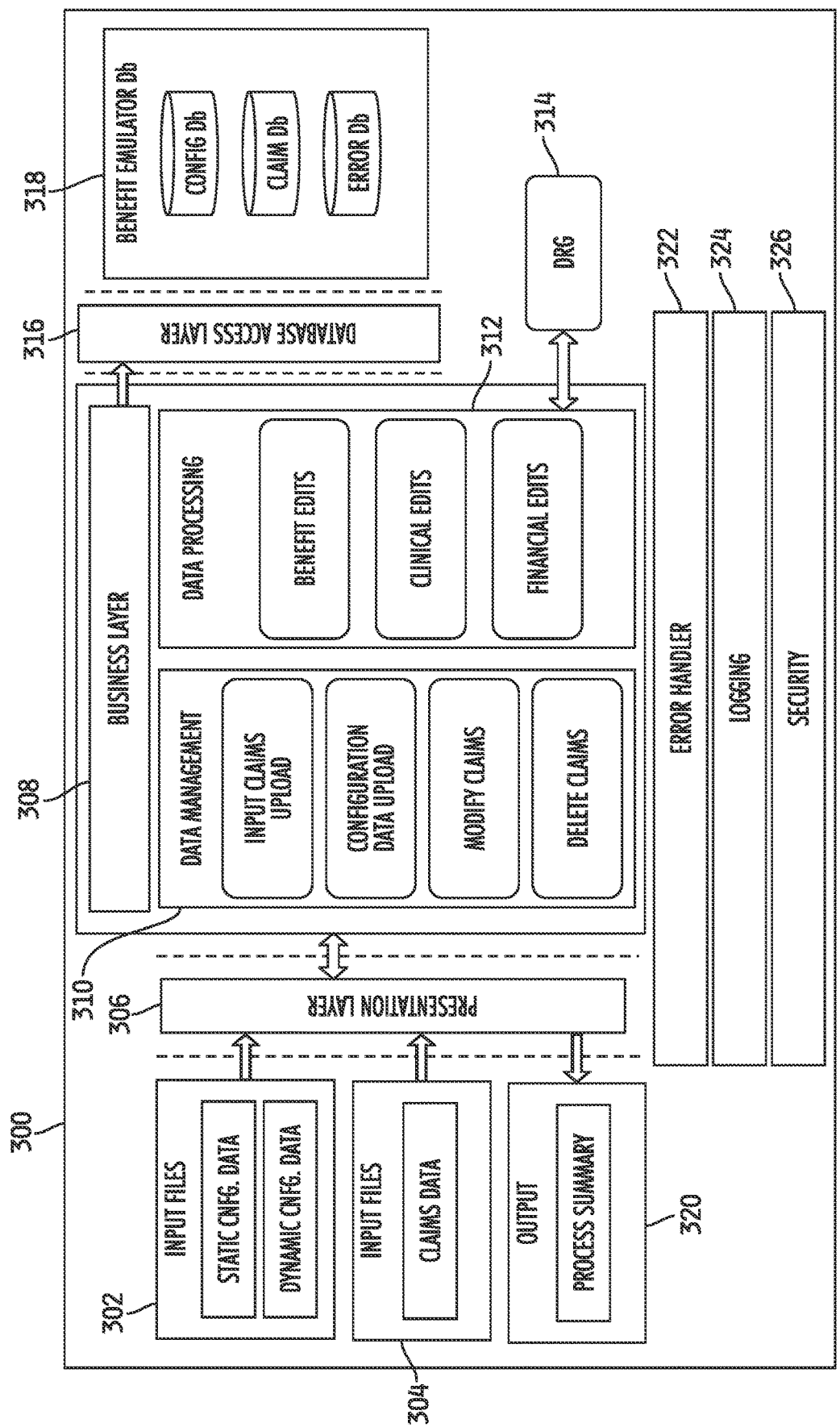
FIG. 3 is a simplified block diagram depicting an architecture of the system illustrated in FIG. 1.

FIG. 3 is a block diagram illustrating the architecture 300 of the medical claim validation tool. The architecture includes, but is not limited to a presentation layer 306, a business layer 308, and a database access layer 316.

The presentation layer 306 provides a user interface to upload static and dynamic configuration data 302 (including benefit, clinical, and financial edits) and medical claim files 304. The presentation layer 306 may illustratively be built using Microsoft Windows Forms using the .NET framework. Through the presentation layer 306, a user may be provided with a summary 320 of the claim status after processing through the benefit emulator system. The presentation layer 306 also handles any exceptions and events are eventually logged into a file to provide a complete trace of an execution process.

The business layer 308 contains components which implement the business logic and rules (e.g., via a rules engine) responsible for the functionality of the medical claim validation tool. These components include, but are not limited to: a data management component 310 and a data processing component 312. Interfacing through the presentation layer 306, the data management component 310 is responsible for uploading claims, uploading configuration data, modifying claims, and deleting claims, as described above with respect to FIG. 2. The data processing component 312 is responsible for application of the benefit edits, clinical edits, and financial edits, to the uploaded claims. To apply the financial edits, the data processing component 312 may also invoke a DRG Grouper, such as "MS-DRG V28" 314. The DRG Grouper 314 is software that classifies medical claims, based on ICD codes and demographic information associated with the medical claims. The business layer 308 also provides access to one or more services including, but not limited to, SQL server integration services for the uploading of the above-described data.

The system supports SQL-based relational database systems such as Oracle and Microsoft-SQL Server, through its database access layer 316. Such a system database 318 acts as a central repository for all configuration, claim, and errored (i.e., rejected) data. Also through the database access layer 316, the system can access any claim validation reports and output (i.e., processed) claim files. The medical claim validation tool architecture also includes an error handler 322 and logging 324 feature, as well as a security feature 326 illustratively in the form of Windows® authentication using an Active Directory and role-based security.

Figure 4:
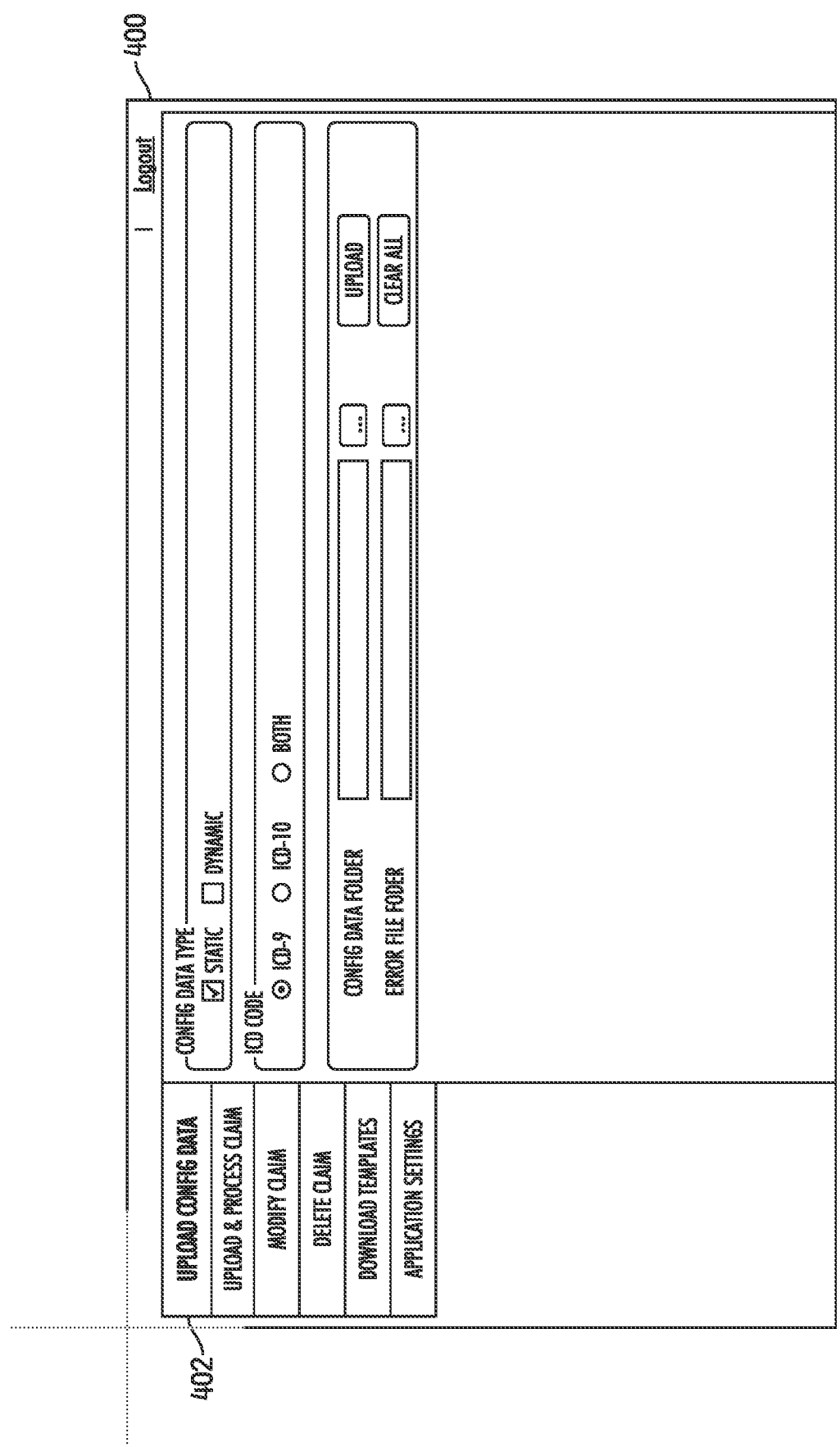
FIG. 4 is an example screen shot illustrating a process for specifying a type of configuration data to be processed by the system of FIG. 1

FIG. 4 is an example screen shot of a user interface 400 for a user to upload 402 configuration data that may be needed to apply benefit, clinical, and/or financial edits. Configuration data includes member, provider, benefit plan, accumulator, clinical, pricing, and other edits that are used by the benefit emulation system to validate the claims. As illustrated in FIG. 4, the configuration data may be static or dynamic, and the user interface 400 provides a selectable interface for making such a selection.

Figure 5:
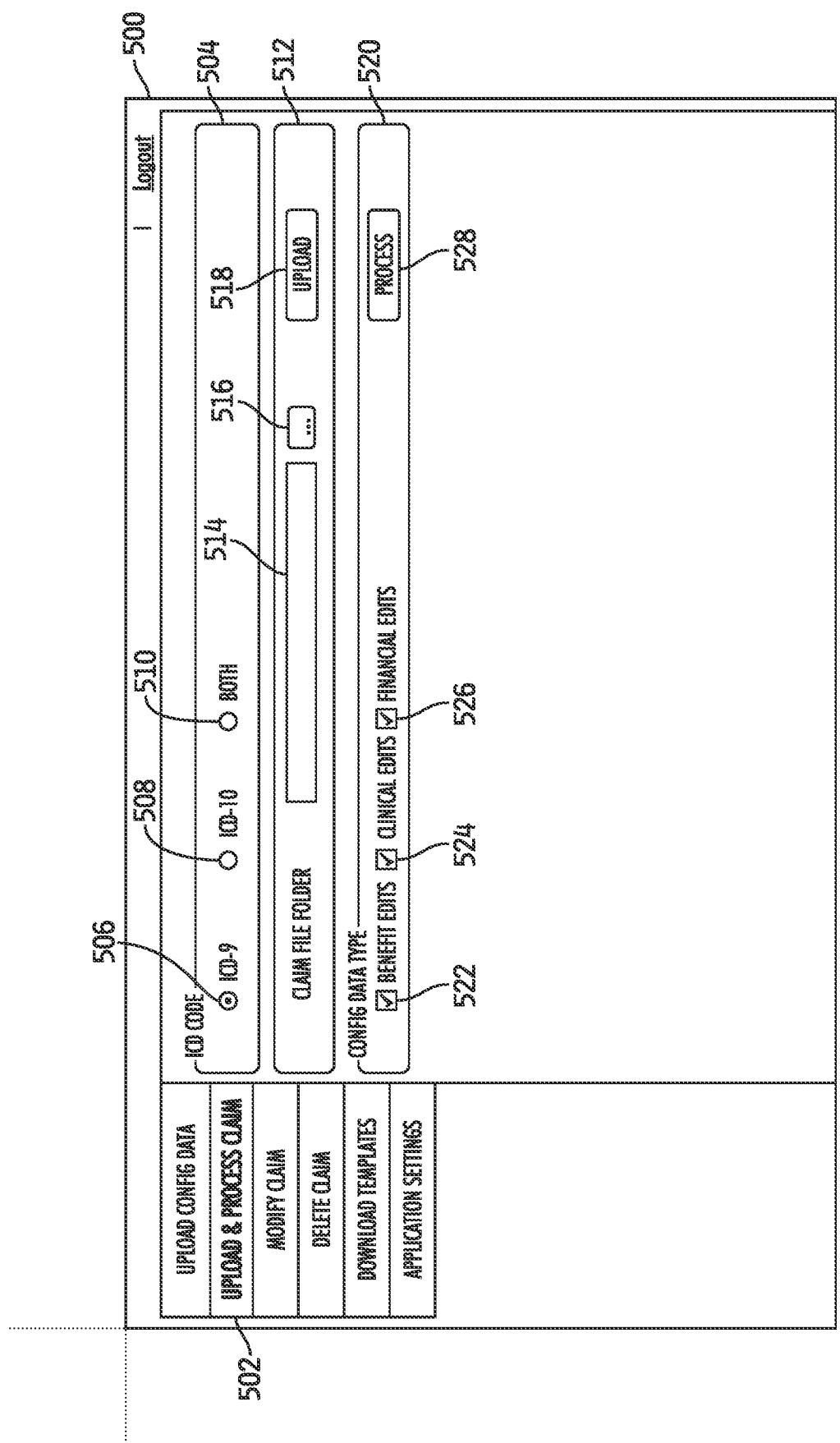
FIG. 5 is an example screen shot illustrating processes for specifying ICD code type and selecting a claim file folder to upload.

FIG. 5 is an example screen shot illustrating a user interface 500 via which a user can upload 502 medical claims data. As used herein, medical claims data includes one or more claim records. A claim record can include data associated with a medical claim. For example, a health care provider can provide services to a patient and a medical claim record can be created for the patient that includes data used to recover payment for medical services. Claim records included in the medical claims data can be patient claim records (e.g., historical claim records) or test claim records that include test data that is not data from an actual patient or a combination of both claim records and test claim records.

The medical claims data can be coded at least in part according to one or more coding systems, such as the above discussed ICD system. A claim record can include data for a Major Diagnostic Category ("MDC") code that is coded according to a MDC coding system version.

As illustrated in FIG. 5, the user interface 500 includes an ICD code entry area 504 via which a user can upload ICD-9 claims 506, ICD-10 claims 508, or both 510. Embodiments of the tool allow the user to select and apply benefit, clinical, and financial edits independently to each of the uploaded claim sets so that each functional area (benefit 522, clinical 524, or financial 526) can be analyzed to understand an impact caused by the ICD-10 code set migration. If desired, the results can also be combined to better understand the holistic impacts on these three areas.

The user interface 500 also includes a claim file upload area 512 including an input window 514 via which the user can specify the location of a claim file to be uploaded. Illustratively, the claim file upload area 512 may also include a browse feature 516 that may be used to browse for locations on the system 100 where claim files may be stored. In any case, the claim file upload area 512 further includes an upload selector 518 that the user may activate to upload the selected claim file.

The user interface 500 also includes a validation activation area 520 at which the user may specify one or more of the edits (522, 524, 526) to invoke, and which further includes a process execution feature 528 via which the user may initiate execution of the validation process.

Figure 6:
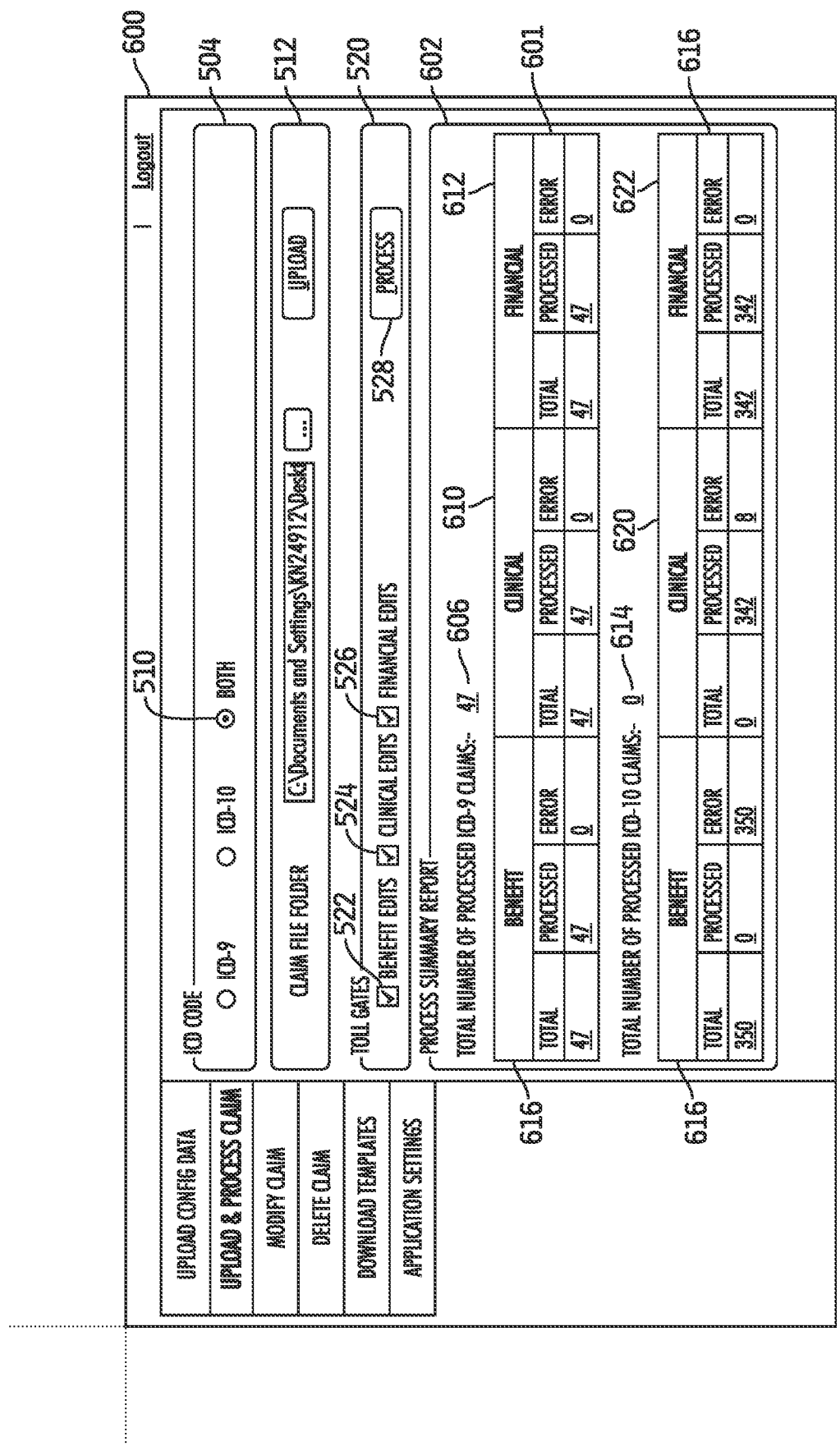
FIG. 6 is an example screen shot illustrating a process for specifying one or more claims processing modules with which to validate claims and further illustrating a summary report of an example result of one such claims validation process.

Once the claim file is validated, the medical claim validation tool provides a summary report providing the status of the claims. FIG. 6 is a screen shot illustrating a user interface 600 containing an example of this report 602. In the example shown, both ICD codes 510 were selected for processing, and each of the benefit edits 522, clinical edits 524 and financial edits 526 were selected prior to selection of the process activation feature 528. The resulting summary report 602 thus includes an ICD-9 result area 604 which includes a benefit result area 608, a clinical result area 610 and a financial result area 612, and an ICD-10 result area 616 which likewise includes a benefit result area 618, a clinical result area 620 and a financial result area 622. The ICD-9 result area 604 shows that each of the benefit module 260, the clinical module 280 and the financial module 270 processed all 47 claims without error, and the total number 606 of processed claims using the ICD-9 code set is therefore 47. The ICD-10 result area 616, on the other hand, shows that the benefit module 260 and the clinical module 280 produced errors, resulting in a total number 614 of zero processed claims using the ICD-10 code set.

Figure 7:
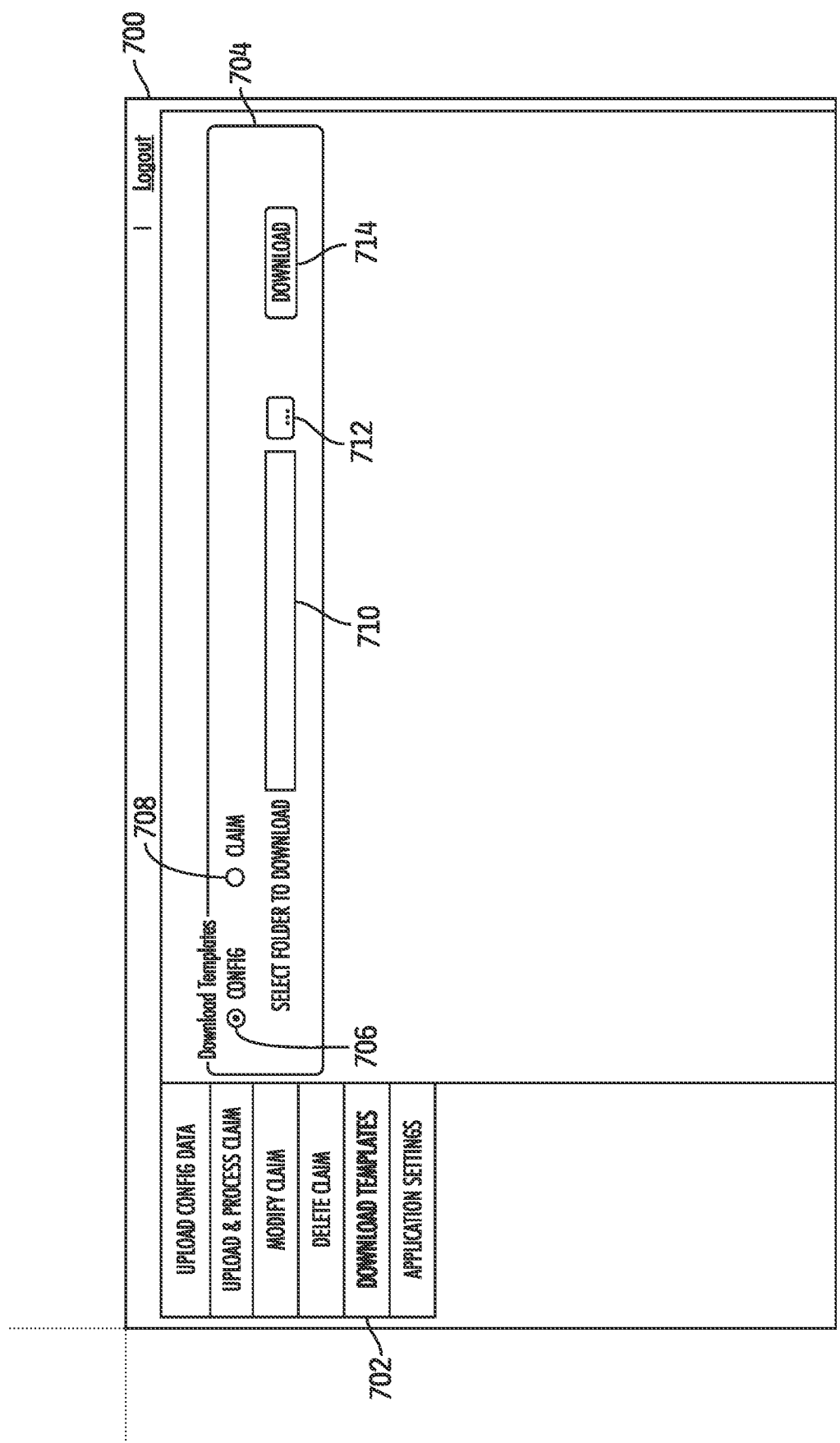
FIG. 7 is an example screen shot illustrating a process for downloading configuration and claim templates for use by the system of FIG. 1.

As shown in an example screenshot in FIG. 7, a user interface 700 includes a template download area 704 via which a user can download 702 templates for uploading his or her respective configuration data 706 and test claims data 708. The template download area 704 includes a window 710 in which the user can enter a download file path, and may also include a browse feature 712 that may be used to browse for potential file storage locations in which to store the downloaded template(s). In any case, the template download area 704 further includes a download feature to that the user may selectively activate to activate template download(s).

Figure 8:
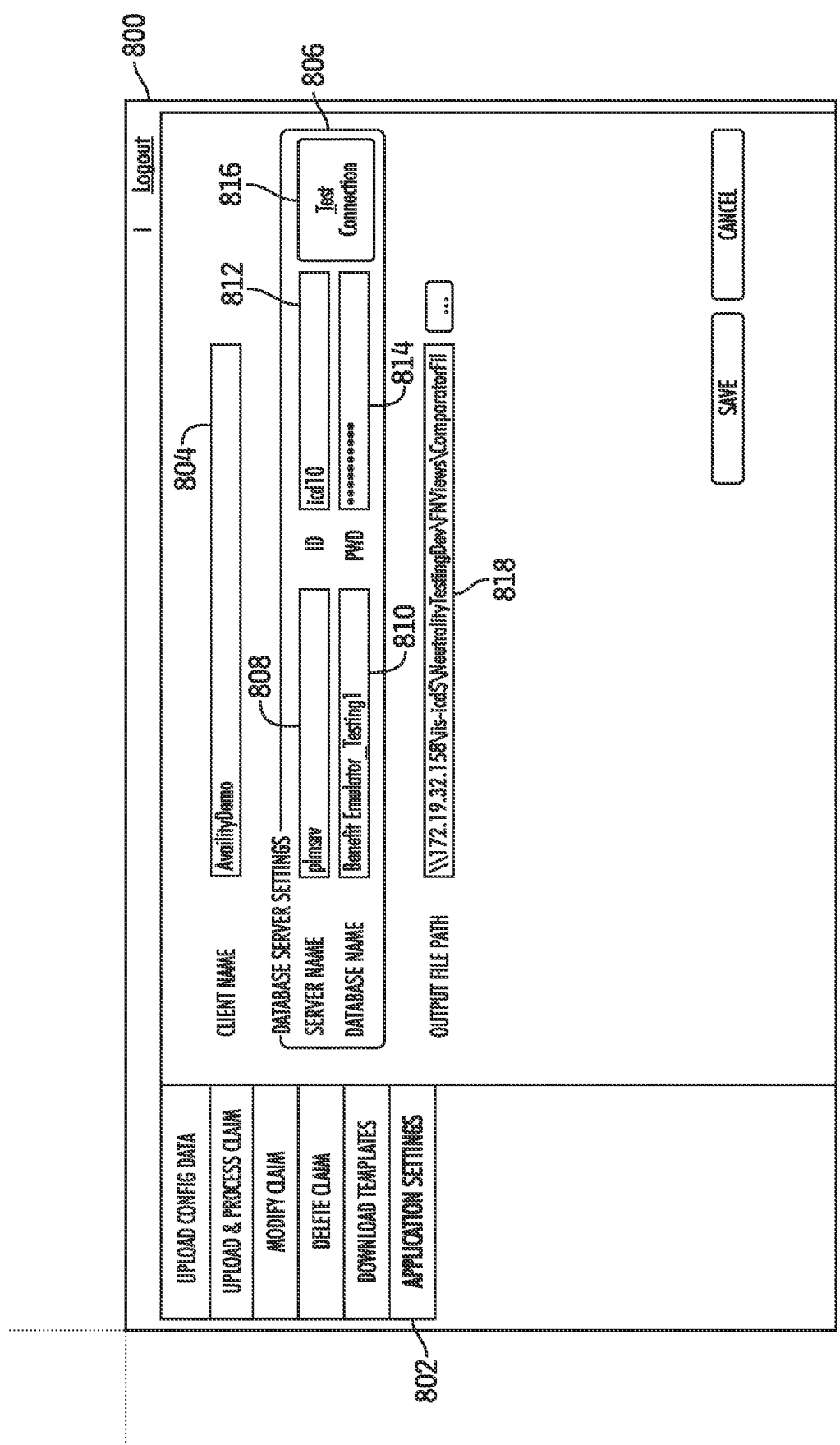
FIG. 8 is an example screen shot illustrating a process for modifying one or more application settings.

As shown in an example screenshot in FIG. 8, a user interface 800 includes features that may be used by the user to modify 802 one or more applications settings. Through the user interface 800, the user can illustratively view and modify a number of different application settings, such as, for example, a client name 804, one or more database server settings 806 such as server name 808, database name 810, identification 812 and password 814. A test connection feature 816 is also included via which the user can selectively test a connection to a selected set of database server settings. The user interface 800 also includes a window in which the user can specify an output file path name.

The system accepts the medical claims data in both header and line forms. Examples of each form are shown in FIGS. 9A and 9B, respectively. FIGS. 10A, 10B, and 10C are examples of benefit, clinical, and financial configuration data, respectively. Illustratively, some such configuration data, such as the clinical and financial configuration data illustrated in FIGS. 10B and 10C, can act as business rules within the medical data validation tool.

As discussed above, the uploaded claims data may be processed; i.e., validated with respect to the edit rules. In one embodiment, the rules may fall into the above discussed three functional areas: benefit rules, clinical rules, and financial rules.

Benefit Rules

According to embodiments of the present disclosure, the medical claim validation tool may employ the use of various benefit claim edit criteria, or rules, to apply to the unprocessed claims. Examples of some such rules include, but are not limited to, validation of an age/gender for a member's covered benefit, whether a service is available for an out of network member, and whether to override a service.

Application of a rule to validate the age of a member's covered benefit illustratively checks whether a member is of a proper age to avail a health care plan's benefits. Specifically, the rule checks to see that the member's age is within the maximum and minimum age requirements specified in the health care plan. For example, as shown in the selected columns of the medical claim data shown in Table I below, the member's age is 38.

TABLE I

| Claim No | Mem Id | Age | Plan | Group | Service Identifier | Reason Code | Status Code |
|---|---|---|---|---|---|---|---|
| C324123 | M363 | 38 | BP101 | GR101 | Patho101 | | |

However, as can be seen in a selected row of covered benefits configuration data shown in Table II below, the age minimum is 0 and the maximum is 35 years of age.

TABLE II

| Benefit Set Identifier | Service Identifier | Age Min | Age Max | Gender | Out Network Allowed | Dep. Allowed |
|---|---|---|---|---|---|---|
| Benefits 1 | Patho101 | 0 | 35 | M | True | True |

Consequently, the claim for this member is rejected by setting the claim status code to "R" and flagged as an error, with an error reason code as shown in field 1001, an example of which is shown in selected columns of the processed claim output in Table III below.

TABLE III

| Claim No | Mem Id | Age | Plan | Group | Service Identifier | Reason Code | Status Code |
|---|---|---|---|---|---|---|---|
| C324123 | M363 | 38 | BP101 | GR101 | Patho101 | ISB06* | R |

The system may display a notes section providing a more detailed explanation of the error code, and an example of this notes section is shown in Table IV below.

TABLE IV

| Term | Source | Description |
| --- | --- | --- |
| ISB06 | Tool (Internal) | Reason code specifying invalid age for availing the benefits |

On the other hand, if the member was 32 years old, according to this example rule, the claim would be accepted and processed, and would move to a next step of validation, (for example, validation with respect to appropriate gender).

Another benefit rule checks whether a certain service is available (or if the service is paid) for an out-of-network member. As used herein, an out-of-network member refers to a member who receives a service from a doctor, hospital, or medical specialist which is not in the member's insurance network of approved providers. Application of this rule verifies that the service category of the claim is allowed for out-of-network members. Tables V, VI and VII below show excerpts from a sample input (unprocessed) claim, configuration data, and an impacted claim (i.e., output), respectively. As shown in Table V, under "Out of network indicator" (ONI) field 1101, "O" indicates the member is an out-of-network member.

TABLE V

| Claim No | Mem Id | Age | Plan | Group | ONI | Service Id | Reas Code | Stat Code |
| --- | --- | --- | --- | --- | --- | --- | --- | --- |
| C324123 | M363 | 38 | BP101 | GR101 | O | Ortho101 | | |

Table VI below, the configuration data field representing whether the selected service is paid for out-of-network members, reads "False".

TABLE VI

| Benefit Set Identifier | Service Identifier | Age Min | Age Max | Gndr | Out Network Allowed | Dependent Allowed |
| --- | --- | --- | --- | --- | --- | --- |
| Benefits 1 | Ortho101 | 0 | 35 | M | False | True |

Therefore, the claim is rejected (Stat Code "R") and recorded as an error with an appropriate reason code (Reas Code ISB08), as shown in the claim output in Table VII.

TABLE VII

| Claim No | Mem Id | Age | Plan | Group | ONI | Service Id | Reas Code | Stat Code |
| --- | --- | --- | --- | --- | --- | --- | --- | --- |
| C324123 | M363 | 38 | BP101 | GR101 | O | Ortho101 | ISB08 | R |

Table VIII below is a sample notes section that may be displayed to provide further explanation for the error code. With this claim recorded as an error, the error claims count increases under the benefit processing report.

TABLE VIII

| Term | Source | Description |
| --- | --- | --- |
| ISB08 | Tool (Internal) | Reason code specifying benefit not covered for out of network |

On the other hand, if the member was "In" the network, or the rules dictated that the service would be covered for an out-of-network member, the claim would be accepted, recorded under this step as a success, and would be forwarded to another validation step (e.g., a check to see if the member's dependents would be covered).

Also as mentioned above, another benefit rule takes the form of an override service. For example, services typically correspond to a medical procedure or treatment performed on a member. However, the payment terms as defined in some contracts can vary based on the complexity of the procedure or treatment. This complexity can be categorized based on additional parameters, such as: the age of the patient, additional diagnosis codes or preexisting conditions of the patient, and any Current Procedural Terminology ("CPT") modifiers. Costlier procedures may require different member sharing requirements as well. As such, payers may handle these requirements using a different service identifier, or override the existing service identifier. For example, Tables IX, X and XI are selected columns of an input claim (header form), input claim (line form), and configuration data from a service definition table, respectively. As can be seen from Table XI, the service is identified as "Radio101" based on the CPT code "76700".

TABLE IX

| Claim No | Mem Id | Gndr | Age | Diag Code1 | Reason Code | Status Code |
| --- | --- | --- | --- | --- | --- | --- |
| C324123 | M363 | M | 62 | 441.4 | | |

TABLE X

| Claim No | Line Number | CPT-HCPCS | No of Units | Service Identifier |
| --- | --- | --- | --- | --- |
| C324123 | 1 | 76700 | 1 | |

TABLE XI

| Procedure Code From | Procedure Code To | Service Identifier |
| --- | --- | --- |
| 76700 | 76705 | Radio101 |

Tables XII and XIII are samples of the corresponding output claim in header form and line form, respectively.

TABLE XII

| Claim No | Mem Id | Diag Code1 | Gender | Age | Claim Reason Code | Claim Status Code |
|---|---|---|---|---|---|---|
| C324123 | M363 | 441.4 | M | 62 | | |

TABLE XIII

| Claim No | Line Number | CPT-HCPCS | No of Units | Service Identifier |
|---|---|---|---|---|
| C324123 | 1 | 76700 | 1 | Radio101 |

Tables XIV, XV and XVI show configuration edit rules, a claim output in header form, and a claim output in line form, respectively, where the override service is applied.

TABLE XIV

| Service Identifier | Diagn code From | Diag Code To | Gndr | Age Min | Age Max | Override Service |
|---|---|---|---|---|---|---|
| Radio101 | 441.4 | 441.4 | M | 60 | 999 | Radio102 |

TABLE XV

| Claim No | Mem Id | Diag Code1 | Claim Reason Code | Claim Status Code |
|---|---|---|---|---|
| C324123 | M363 | 441.4 | | |

TABLE XVI

| Claim No | Line Number | CPT-HCPCS | No of Units | Service Identifier |
|---|---|---|---|---|
| C324123 | 1 | 76700 | 1 | Radio102 |

For example, as shown in the configuration edit rule in Table XIV, the override service reads "Radio 102" for the associated diagnosis code "441.4". This may be applied to the claim, and, in turn, the service "Radio 101" is overridden to now be "Radio 102" as shown in the claim line output in Table XVI. Table XVII is a sample notes section that the system may include to provide further explanation for the noted service override.

TABLE XVII

| Term | Source | Description |
|---|---|---|
| Radio101 | Tool (Internal) | Service identifiers referring to General radiology |
| 441.4 | ICD-9 Diagnosis | Abdominal aortic aneurysm (bulging of aortic nerve passing through Abdomen) |
| Radio102 | Tool (Internal) | Radiology payment included in Medical Service |

Clinical Edits

In some embodiments, the system employs the use of various clinical edit rules to apply the input claims data to. Among other things, application of these rules checks that a claim's identified procedure has an appropriate diagnosis code as well as whether a provider's specialty is appropriate for the identified procedure code.

For example, a rule to validate an appropriate procedure with a given diagnosis code checks if the procedure code listed on the claim is appropriate for the given diagnosis code. This rule ensures that at least one valid diagnosis code is present for the procedure code on the input claim. If there is no matching diagnosis code for the subject procedure, the system rejects the claim, and records it as an error. If successfully validated, however, the claim is forwarded on to determine if the age criteria are met for the diagnosis code.

In the case of a failure, the error count increases under the benefit processing summary. As an example, Tables XVIII, XIX and XX show select columns from a sample input (i.e., unprocessed) claim, configuration data from a diagnosis clinical eligibility table, and select columns from a sample output respectively. As shown in the input claim of Table XVIII below, the procedure code of "00.83" displays a corresponding diagnosis code of "276.1".

TABLE XVIII

| Claim No | Mem Id | Diag Code1 | Diag Code 2 | Proc Code 1 | Proc Code 2 | Svc Id | Reas Code | Status Code |
|---|---|---|---|---|---|---|---|---|
| C324123 | M363 | 414.01 | 276.1 | 00.66 | 00.83 | Cardio101 | | |

Referring to Table XIX below, the edit rules dictate that, for a procedure code of "00.83", the diagnosis code must be a number between "836.0" to "836.69".

TABLE XIX

| Diagnosis Code From | Diagnosis Code To | Age Min | Age Max | Gender | Procedure code from | Procedure Code To |
|---|---|---|---|---|---|---|
| 414.01 | | | | | | 00.66 |
| 276.1 | | | | | | 00.66 |
| 836.0 | 836.69 | | | | | 00.83 |

As such, the claim is counted as an error according to this rule, resulting in an output as shown in Table XX below.

TABLE XX

| Claim No | Mem Id | Age | Plan | Group | ONI | Service Identifier | Reason Code | Status Code |
|---|---|---|---|---|---|---|---|---|
| C324123 | M363 | 38 | BP101 | GR101 | O | Cardio101 | IDG01* | R |

Table XXI below shows a sample notes section that the system may display to provide further explanation for the subject reason code, diagnosis codes, and procedure codes.

TABLE XXI

| Term | Source | Description |
|---|---|---|
| 00.66 | ICD-9 Procedure Code | Percutaneous transluminal coronary angioplasty (PTCA) |
| 00.83 | ICD-9 Procedure Code | REV KNEE REPLACE-PATELLA (Knee Replacement) |

TABLE XXI-continued

| Term | Source | Description |
|---|---|---|
| 414.01 | ICD-9 Diagnosis | Coronary Atherosclerosis (Blockage of Coronary Artery) |
| 276.1 | ICD-9 Diagnosis | Hyposmolality (Excessive fluid and low sodium) |
| IDG01 | Benefit Emulators Internal | Reason code specifying that required diagnosis is missing on claims file |

Next, as mentioned above, application of another rule checks whether a provider with the appropriate qualifications had performed the noted procedure. This rule ensures that "provider specialty" input on the claim matches the provider's specialty according to the rule reflected in the configuration data. If there is a match, the claim is deemed successful. However, if no match is found, (e.g., the provider failed to have the required qualifications), the claim is deemed an error with an appropriate reason code, which will increase the associated error count. As an example, Tables XXII, XXIII and XXIV show a sample input claim, configuration edit data from a procedure clinical eligibility table, and a sample output, respectively. As shown by the input claim in Table XXII below, the provider performing the procedure having the code "36.07" has a Physical Medicine and Rehabilitation specialty denoted "PHY".

TABLE XXII

| Claim No | Mem Id | Diag Code1 | Diag Code 2 | Pro Cde 1 | Pro Cde 2 | Prov Spclty | Svc Id | Reas Cde | Stat Cde |
|---|---|---|---|---|---|---|---|---|---|
| C324123 | M363 | 414.01 | 276.1 | 0.66 | 36.07 | PHY | Cardio101 | | |

However, as shown in the clinical edit rules of Table XXIII below, for procedure code "36.07", the provider needs to have a Cardiology specialty. In other words, the procedure needed to be performed by a cardiologist for the claim to be deemed successful.

TABLE XXIII

| Procedure code from | Procedure Code To | Age Min | Age Max | Gender | Modifier | Provider Specialty |
|---|---|---|---|---|---|---|
| 00.66 | | 15 | 40 | | | |
| 00.66 | | 15 | 40 | | | |
| 00.66 | | | | | | Cardiologist |
| 36.07 | | | | | | Cardiologist |

Accordingly, an output as shown in Table XXIV below may result in an error code "IPSO1", and the claim is rejected by the system.

TABLE XXIV

| Claim No | Mem Id | Age | Plan | Group | ONI | Service Identifier | Reason Code | Status Code |
|---|---|---|---|---|---|---|---|---|
| C324123 | M363 | 38 | BP101 | GR101 | O | Patho101 | IPS01* | R |

Table XXV below is a sample notes section that the system may include to provide further explanation for the subject error code, diagnosis codes, and procedure codes.

TABLE XXV

| Term | Source | Description |
|---|---|---|
| 00.66 | ICD-9 Procedure Code | Percutaneous transluminal coronary angioplasty (PTCA) |
| 36.07 | ICD-9 Procedure Code | INS DRUG-ELUT CORONRY ST (Insertion of Coronary Stem) |
| 414.01 | ICD-9 Diagnosis Code | Coronary Atherosclerosis (Blockage of Coronary Artery) |
| 276.1 | ICD-9 Diagnosis Code | Hyposmolality (Excessive fluid and low sodium) |
| IPS01 | Tool (Internal) | Reason code specifying that provider specialty does not match the requirement |

Financial Edits

To determine an amount to pay for a billed medical claim, providers often use a standard set of codes called Medicare Severity Diagnosis-Related Group ("MS-DRG") codes, which are based on ICD codes. These MS-DRG or simply "DRG" codes allow hospitals to bill health insurance plans and Medicare for services. Hospitals are typically paid a set fee for treating all patients in a single DRG, regardless of the actual cost for that case. Each DRG is assigned a weight. The weight is used to adjust for the fact that different types of patients consume different resources and have different costs. Groups of patients who are expected to require above average resources have a higher weight than those who require fewer resources.

To arrive at the reimbursement that a hospital (or other health care provider) will receive for a particular DRG, the hospital's base rate is multiplied by the DRG weight. In the most simplified terms, the hospital base rate identifies the reimbursement that a hospital would receive for treating the average patient. The MS-DRGs range from 001-999, with many unused numbers to accommodate future MS-DRG expansion.

One MS-DRG is assigned to each inpatient stay. The DRGs are assigned using the principal diagnosis and additional diagnoses, the principal procedure and additional procedures, sex and discharge status. Diagnoses and procedures assigned by using ICD-9 codes determine the DRG assignment. Accurate and complete ICD-9 coding is essential for correct MS-DRG assignment and subsequent reimbursement.

Embodiments of the present disclosure apply financial edits to perform certain calculations, such as allowed amounts and other calculations related to these DRG codes. For example, the system may interface with Medical Severity (MS)-DRG software to extract DRG information. As used herein, the DRG calculation is part of the allowed amount calculation, which may be necessary to evaluate member liability amounts. As used herein, the "allowed amount" refers to the total amount of money that the medical care provider can ultimately receive. It is a combination of the amount the insurance will pay plus the amount for which the patient is responsible. Simply put, the calculation is the following:

allowed amount=patient responsible amount+insurance payment

As an example application of these financial edits, Tables XXVI and XXVII show select columns of an input claim and output claim, respectively. The input claim in Table XXVI below has a first diagnosis code "414.01," a second diagnosis code "276.01," a first procedure code "0.66" and a second procedure code "36.07." These parameters are subject to the DRG code calculation.

TABLE XXVI

| Claim No | Mem Id | Diag Cde1 | Diag Cde 2 | Proc Cde1 | Proc Cde 2 | DRG Code | DRG wt | MDC Code |
|---|---|---|---|---|---|---|---|---|
| C324123 | M363 | 414.01 | 276.1 | 0.66 | 36.07 | | | |
| C324123 | M363 | 414.01 | 276.1 | 0.66 | 36.07 | | | |

An output, as shown in Table XXVII below, may result in displaying a DRG code "247," DRG weight "1.9691, and MDC code "05".

TABLE XXVII

| Claim No | Mem Id | Diag Cde1 | Diag Cde 2 | Proc Cde1 | Proc Cde2 | DRG Code | DRG wt | MDC Code |
|---|---|---|---|---|---|---|---|---|
| C324123 | M363 | 414.01 | 276.1 | 0.66 | 36.07 | 247 | 1.9691 | 05 |

Another possible financial edit is the member liability calculation which is based on the allowed amounts. For this edit, the following amounts are calculated: individual deductible, co-insurance, and co-pay. Members' cost sharing parameters are loaded into the benefit emulator tool as a part of configuration data, and the above amounts are calculated, an example output reflecting these amounts is shown in Table XXVIII below.

TABLE XXVIII

| Benefit set Id | Service Id | INN Copay | INN Coins | INN Ded | OON Copay | OON Coins | OON Ded |
|---|---|---|---|---|---|---|---|
| Benefits1 | Patho101 | 10 | 10 | 20 | 20 | 20 | 40 |

While the disclosure has been illustrated and described in detail in the drawings and foregoing description, such an illustration and description is to be considered as exemplary and not restrictive in character, it being understood that only illustrative embodiments have been shown and described and that all changes and modifications consistent with the disclosure and recited claims are desired to be protected.

What is claimed is:

1. A computerized method for validating medical claim data, the computerized method comprising:
receiving a first and second medical claim, each respectively associated with a first and a second healthcare classification system;
receiving claim edit criteria comprising providing a user interface for receiving configuration data including the claim edit criteria, wherein the claim edit criteria comprises one of a benefit or clinical rule configured to validate one of the medical claims, wherein each of the benefit or clinical rule comprises a healthcare payer policy requirement;
storing the first and second medical claims in association with the first and the second classification systems, respectively, said storing comprising testing a connection associated with a selected set of database server settings upon receiving a user test connection input;
validating the stored medical claims by applying each of the benefit rule and the clinical rule of the received claim edit criteria independently to each of the stored first and second medical claims and to the associated classification system so that each of the benefit rule and the clinical rule are validated independently for each of said first and second healthcare classification systems, wherein the validating step further comprises:
determining if the at least one of the stored medical claims meets the healthcare payer policy requirement of the benefit or clinical rule; and
rejecting the at least one of the stored medical claims if the at least one of the stored medical claims does not meet the healthcare payer policy requirement of the benefit or clinical rule; and
graphically displaying selected results of the validating, wherein said clinical rule comprises stored medical procedure qualification information associated with a medical service provider indicative of whether or not said medical service provider has a medical specialty that matches a clinical eligibility criterion for a procedure code identified in each of said first and second store medical claims.

2. The computerized method of claim 1, further comprising, upon validating of the stored medical claim, accepting the stored medical claim as a processed claim.

3. The computerized method of claim 1, wherein the claim edit criteria include a maximum and minimum age healthcare payer policy requirement corresponding to a service provided to the member.

4. The computerized method of claim 1, wherein the claim edit criteria include an availability of a service provided to the member healthcare payer policy requirement, wherein the member is an out-of-network member.

5. The computerized method of claim 1, wherein the claim edit criteria include a valid procedure code corresponding to a diagnosis code healthcare payer policy requirement.

6. The computerized method of claim 1, wherein the user interface for receiving configuration data comprises a mechanism configured to allow the user to upload the configuration data including the claim edit criteria comprising the one of the benefit, or clinical rule configured to validate one of the medical claims and further comprising the benefit or clinical rule healthcare payer policy requirement.

7. The computerized method of claim 1, wherein the claim edit criteria further comprises a financial rule comprising a healthcare payer policy requirement.

8. The computerized method of claim 7, further wherein the validating step further comprises:
    determining if the at least one of the stored medical claims meets the healthcare payer policy requirement of the financial rule; and
    rejecting the at least one of the stored medical claims if the at least one of the stored medical claims does not meet the healthcare payer policy requirement of the financial rule.

9. A system for validating medical claim data of a member, the computerized system comprising:
    one or more computing devices including a memory having program code stored therein and a processor in communication with the memory for carrying out instructions in accordance with the stored program code, wherein the program code, when executed by the processor, causes the processor to:
    receive a first and second medical claim, each respectively associated with a first and a second healthcare classification system;
    receive claim edit criteria comprising providing a user interface for receiving configuration data including the claim edit criteria, wherein the claim edit criteria comprises one of a benefit or clinical rule configured to validate one of the medical claims, wherein each of the benefit or clinical rule comprises a healthcare payer policy requirement;
    store the first and second medical claims in association with the first and the second classification systems, respectively, said storing comprising testing a connection associated with a selected set of database server settings upon receiving a user test connection input;
    validate the stored medical claims by applying each of the benefit rule and the clinical rule of the received claim edit criteria independently to each of the stored first and second medical claims and to the associated classification system so that each of the benefit rule and the clinical rule are validated independently for each of said first and second healthcare classification systems, the program code further causes the processor to:
        determine if the at least one of the stored medical claims meets the healthcare payer policy requirement of the benefit or clinical rule; and
        reject the at least one of the stored medical claims if the at least one of the stored medical claims does not meet the healthcare payer policy requirement of the benefit or clinical rule; and
    graphically display selected results of the validating,
    wherein said clinical rule comprises stored medical procedure qualification information associated with a medical service provider indicative of whether or not said medical service provider has a medical specialty that matches a clinical eligibility criterion for a procedure code identified in each of said first and second stored medical claims.

10. The system of claim 9, wherein the program code, when executed by the processor, further causes the processor to accept the stored medical claim as a processed claim upon the stored medical claim meeting the claim edit criteria validation.

11. The system of claim 9, wherein the claim edit criteria include a maximum and minimum age healthcare payer policy requirement corresponding to a service provided to the member.

12. The system of claim 9, wherein the claim edit criteria include an availability of a service provided to the member healthcare payer policy requirement, wherein the member is an out-of-network member.

13. The system of claim 9, wherein the claim edit criteria include a valid procedure code corresponding to a diagnosis code healthcare payer policy requirement.

14. The computerized system of claim 9, wherein the claim edit criteria further comprises a financial rule comprising a healthcare payer policy requirement.

15. The computerized method of claim 14, wherein to complete the validation, the program code further causes the processor to:
    determine if the at least one of the stored medical claims meets the healthcare payer policy requirement of the financial rule; and
    reject the at least one of the stored medical claims if the at least one of the stored medical claims does not meet the healthcare payer policy requirement of the financial rule.

16. A non-transitory computer readable medium upon which is embodied a sequence of programmed instructions which, when executed by a processor, cause the processor to perform steps comprising:
    receiving a first and second medical claim, each respectively associated with a first and a second healthcare classification system;
    receiving claim edit criteria comprising providing a user interface for receiving configuration data including the claim edit criteria, wherein the claim edit criteria comprises one of a benefit or clinical rule configured to validate one of the medical claims, wherein each of the benefit or clinical rule comprises a healthcare payer policy requirement;
    storing the first and second medical claims in association with the first and the second classification systems, respectively, said storing comprising testing a connection associated with a selected set of database server settings upon receiving a user test connection input;
    validating the stored medical claims by applying each of the benefit rule and the clinical rule of the received claim edit criteria independently to each of the stored first and second medical claims and to the associated classification system so that each of the benefit rule and the clinical rule are validated independently for each of said first and second healthcare classification systems, wherein the code for validating further comprises:
        determining if the at least one of the stored medical claims meets the healthcare payer policy requirement of the benefit or clinical rule; and rejecting the at least one of the stored medical claims if the at least one of the stored medical claims does not meet the healthcare payer policy requirement of the benefit or clinical rule; and graphically displaying selected results of the validating, wherein said clinical rule comprises stored medical procedure qualification information associated with a medical service provider indicative of whether or not said medical service provider has a medical specialty that matches a clinical eligibility criterion for a procedure code identified in each of said first and second stored medical claims.

17. The non-transitory computer readable medium of claim 16, further comprising accepting the stored medical claim as a processed claim upon the stored medical claim meeting the claim edit criteria validation.

18. The computer program product of claim 16, wherein the claim edit criteria include a maximum and minimum age healthcare payer policy requirement corresponding to a service provided to the member.

19. The computer program product of claim 16, wherein the claim edit criteria include an availability of a service provided to the member healthcare payer policy requirement, wherein the member is an out-of-network member.

20. The computer program product of claim 16, wherein the claim edit criteria further comprises a financial rule comprising a healthcare payer policy requirement.

21. The non-transitory computer readable medium of claim 20, wherein the validating further comprises:

determining if the at least one of the stored medical claims meets the healthcare payer policy requirement of the financial rule; and rejecting the at least one of the stored medical claims if the at least one of the stored medical claims does not meet the healthcare payer policy requirement of the financial rule.

* * * * *